United States Patent [19]

Usui

[11] Patent Number: 4,846,568

[45] Date of Patent: Jul. 11, 1989

[54] METHOD OF ANALYZING AN ELECTRORETINOGRAM

[75] Inventor: Shiro Usui, Godo-Shukusha Takashi-Jutaku 5-504, 1, 2-chome, Aza-Higashiura, Kitayama-cho, Toyohashi-shi, Aichi-ken, Japan

[73] Assignees: Shiro Usui; Toyo Medical Co., Ltd., both of Aichi, Japan

[21] Appl. No.: 172,242

[22] Filed: Mar. 23, 1988

[30] Foreign Application Priority Data

Mar. 28, 1987 [JP] Japan .................................. 62-75220
Mar. 15, 1988 [JP] Japan .................................. 63-60738

[51] Int. Cl.$^4$ .......................... A61B 3/14; A61B 3/10; A61B 3/02
[52] U.S. Cl. .................................. 351/246; 351/205; 351/211; 351/243; 128/745
[58] Field of Search ............... 351/205, 211, 243, 246; 128/745

[56] References Cited

U.S. PATENT DOCUMENTS 4,676,611 6/1987 Nelson et al. .................... 351/211 X Primary Examiner—Rodney B. Bovernick
Attorney, Agent, or Firm—Oliff & Berridge

[57] ABSTRACT

A method of separating an oscillatory potential wave from an electroretinogram of a subject which contains an "a" wave, a "b" wave and said oscillatory potential wave that overlap each other. The electroretinogram ([1]) is produced by light stimulation to the retina of an eye of the subject, and is detected by a suitable device. The peak-to-peak distances of the detected electroretinogram are determined, and a mean period (T) of the oscillatory potential wave ([10]) to be separated from said electroretinogram is obtained. Then, a tentative start point (A) of the oscillatory potential wave is determined, and an OP-free waveform ([7], [9]) free of said oscillatory potential wave is obtained by obtaining moving averages of a first intermediate waveform ([6], [8]) which is determined based on the electroretinogram and the determined tentative start point (A). The oscillatory potential wave ([10]) is extracted by subtracting the OP-free waveform ([7], [9]) from the electroretinogram ([1]).

6 Claims, 8 Drawing Sheets

FIG.1
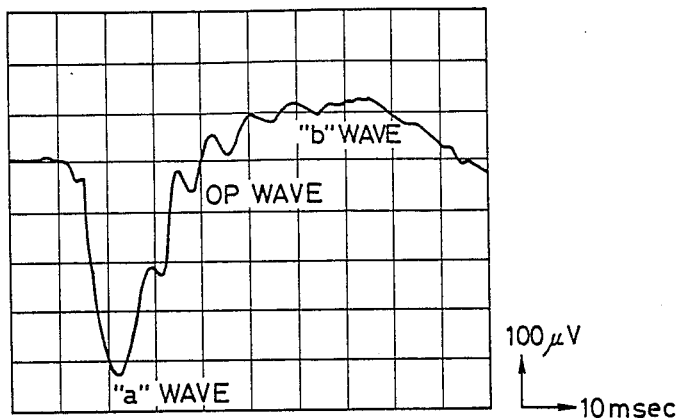
FIG.2(a) PRIOR ART    TIME CONSTANT= 0.1 SEC. FOR "a" AND "b" WAVES
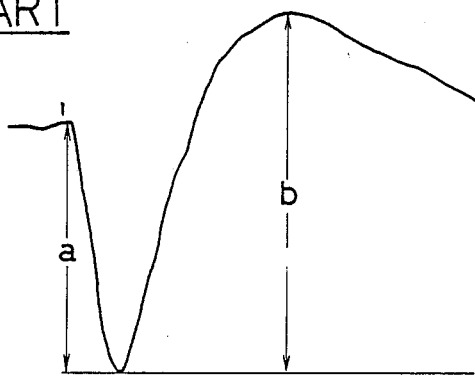
FIG.2(b) PRIOR ART    TIME CONSTANT =0.003 SEC. FOR OP COMPONENT
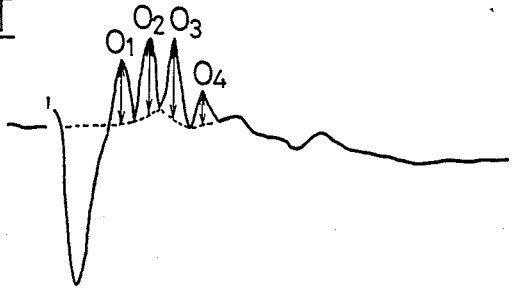

[1] ERG WAVEFORM
[2] DIFFERENTIATED ERG WAVEFORM

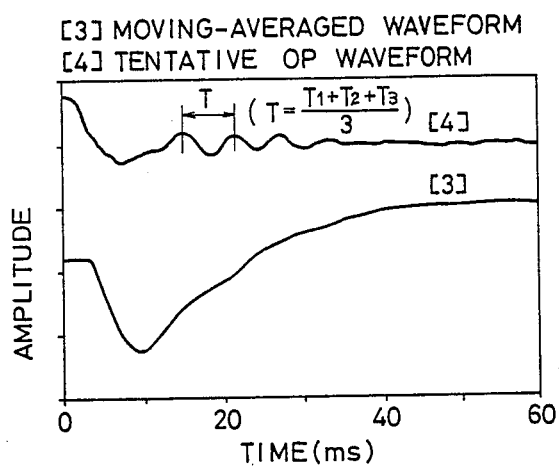
FIG.6 MOVING-AVERAGED WAVEFORM
[4] TENTATIVE OP WAVEFORM
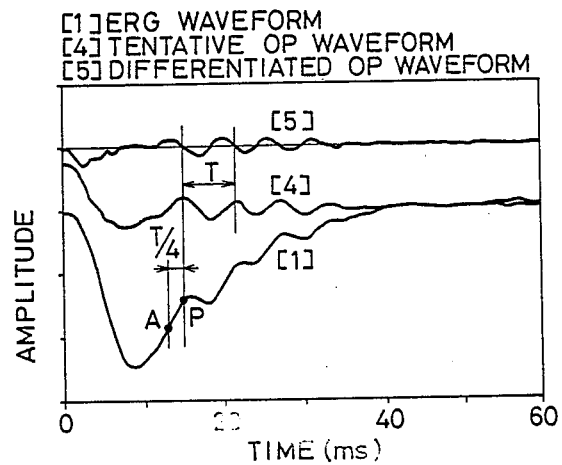
FIG.7 ERG WAVEFORM
[4] TENTATIVE OP WAVEFORM
[5] DIFFERENTIATED OP WAVEFORM
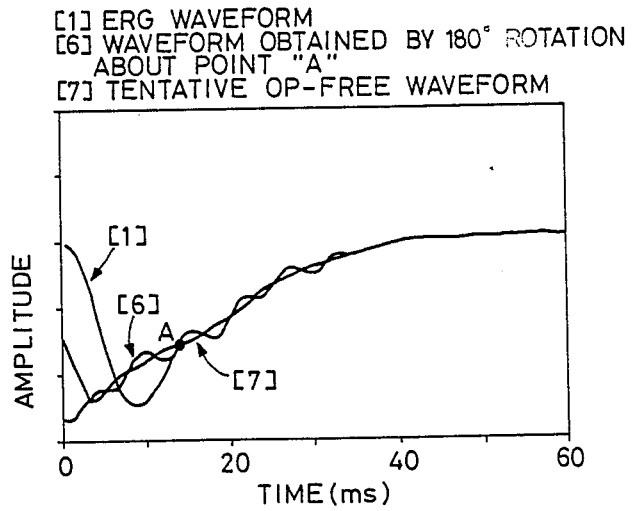
FIG.8 ERG WAVEFORM
[6] WAVEFORM OBTAINED BY 180° ROTATION ABOUT POINT "A"
[7] TENTATIVE OP-FREE WAVEFORM

METHOD OF ANALYZING AN ELECTRORETINOGRAM

BACKGROUND OF THE INVENTION

1. Field of the Invention

The present invention relates in general to a method of analyzing an electroretinogram, and more particularly to a method of extracting or separating an oscillatory potential component from the electroretinogram and measuring various parameters of the separated OP component, by processing the detected electroretinogram, based on electrophysiological knowledge and findings, without conventionally available electrical, mechanical or manual processing techniques.

2. Discussion of the Prior Art

An electroretinogram (hereinafter abbreviated as "ERG" when appropriate) is a graphic record of the manner in which a potential developed by retina cells of the eye in response to a flash light stimulus varies with time. The potential is developed between the cornea and the forehead (or chin or cheek). Basically, the ERG consists of three major components, i.e., an "a" wave, a "b" wave and an oscillatory potential wave (hereinafter abbreviated as "OP wave", or referred to as "OP component" or "OP component wave" as appropriate), as shown in FIG. 1. The ERG response to a light stimulus is considered a sum of potentials which are induced by various cells of the retina of the eye. Described more specifically, the "a" wave is a result of a response of the visual cells and the "b" wave is a result of a response of the Muller cells, while the OP wave is a result of a response of the Amacrine cells.

Since it is impossible to directly observe or record responses of the various retina cells of the human eyes, an ERG or electroretinography is a very effective way of obtaining data representative of the functioning conditions of the retina cells. In recent years, therefore, the ERG is widely utilized for many varied clinical purposes, for example, for diagnosis or determination of ocular pathology such as opaque intermediate media or vitreous, and retinopathy, and for inspection of the visual function of infant. In particular, it is known that the OP component of an ERG detected on a subject suffering from diabetes, Behcet syndrome or other diseases has a tendency of declining or disappearing even in a relatively early stage of development of such diseases. Accordingly, the OP component of the ERG is useful for finding such diseases at a relatively initial period of development thereof.

There are known some methods of separating and analyzing the oscillatory potential or OP component from a detected ERG. For instance, a filter is used to process a detected ERG response, and different time constants of the filter are used to detect the "a" and "b" waves and to detect the OP component, so that the OP component as distinguished from the "a" and "b" waves is amplified, as indicated in FIGS. 2(a) and 2(b). The obtained OP component provides an aid for the empiric determination of diseases, based on a relation between the waveform of the OP component and the diseases. The OP component of the detected ERG is manually processed to measure various characteristic parameters of the OP component wave, as indicated in FIG. 3, such as: amplitudes O1, O2, etc. which are distances between straight lines connecting adjacent negative peaks of the OP wave, and positive peaks of the same; latency times Dp, Db between a moment of light stimulation to the retina and the first positive and negative peaks of the OP wave, respectively; and time durations T1, T2, T3, t1, t2 between the adjacent peaks. An alternative method to measure the OP component is accomplished by linearly interpolating midpoints of the amplitude of the OP wave and thereby separating the "b" wave, and subtracting the "b" wave from the detected or measured ERG.

However, the known electric, mechanical or manual methods of extracting and analyzing the OP component or wave of an ERG are not accurate enough for objective determination or analysis in clinical diagnosis, and suffers from several problems in their practice. Stated in greater detail, the "a" wave, "b" wave and OP component wave of an ERG which have different latency times (times delays) after the moment of light stimulation overlap each other in a complicated fashion in the axis of time. Further, in the power spectrum of a typical ERG, the OP wave and "a" and "b" waves which are signals having peaks in a relatively narrow frequency band in the neighborhood of one hundred and several tens of Hz, overlap each other, in the axis of frequency, as indicated in FIG. 4. Hence, the relatively simple conventional methods are inherently incapable of accurately extracting and analyzing the OP component. While there have been attempts in the field of engineering to analyze the ERG in terms of the frequencies of the components, such attempts are not practically accurate and reliable from the clinical or physiological standpoint, for objective analysis of the ERG and determination of the parameters of its OP component which represent ocular pathology or retinopathy and related diseases.

SUMMARY OF THE INVENTION

It is therefore an object of the present invention to provide a method of accurately separating an oscillatory potential component from an electroretinogram which contains "a" and "b" waves, so that a clinical analysis of a subject can be accomplished based on the parameters of the obtained oscillatory potential component.

The above object can be achieved according to the principle of the present invention, which provides a method of separating an oscillatory potential wave from an electroretinogram of a subject which contains an "a" wave, a "b" wave and the oscillatory potential wave that overlap each other, the method comprising the steps of: detecting the electroretinogram which is produced by light stimulation to the retina of an eye of the subject; determining peak-to-peak distances of the electroretinogram, and thereby obtaining a mean period of the oscillatory potential wave to be separated from the electroretinogram; determining a tentative start point of the oscillatory potential wave; obtaining an OP-free waveform free of the oscillatory potential wave, by obtaining moving averages of an intermediate waveform which is determined based on the electroretinogram and the determined tentative start point; and extracting the oscillatory potential wave by subtracting the OP-free waveform from the electroretinogram.

The present method according to the invention described above was developed as a result of extensive research, study and analysis on an electroretinogram, based on electrophysiological knowledge and findings of the present inventors, that (a) an electroretinogram consists of a sum of three component waves which have different latency times with respect to the moment of light stimulation to the retina of the eye; that (b) while the "a" and "b" waves have considerably smooth or gentle curves (i.e., have considerably low frequencies) as compared with that of the oscillatory potential wave or OP wave, these "a" and "b" waves overlapping each other cooperate to form negative peaks having comparatively high frequency components which overlap the frequency components of the OP wave; that (c) the OP wave has a relatively fixed or constant start point; and that (d) the OP wave has a relatively high degree of periodicity in a comparatively narrow band. Based on the above knowledge and findings, the instant method is adapted to process ERG waveform data during actual measurement or detection of the ERG, by way of obtaining moving averages of, and by differentiation of the ERG data, so as to extract the oscillatory potential or OP component of the REG which overlaps the "a" and "b" waves. Determination on the subject from which the ERG is detected can be achieved with high precision, based on the characteristic parameters of the thus extracted OP component of the ERG.

As describe above, the method according to the instant invention, which is practiced upon measurement of an electroretinogram (ERG), permits accurate separation or retrieval of an oscillatory potential wave from an electroretinogram, utilizing the moving-average and differentiation processing of the measured ERG, in light of the relatively constant or non-fluctuating start point or beginning of the OP wave, and the relatively high periodicity of the OP wave in a comparatively narrow band. The above separation is possible even though the OP wave and the "a" and "b" waves of the ERG have different latency times or delays from the moment of light stimulation of the retina cells, and overlap each other in the axis of time.

In the conventional method using an electric filter to extract or amplify only the OP wave, the extracted OP component tends to undesirably contain portions of the "a" and "b" waves, since the OP wave and the "a" and "b" waves are relatively narrow frequency band signals which have peaks around one hundred and several tens of Hz, and which overlap each other in the axis of frequency in the power spectrum of the ERG. According to the present invention, however, only the oscillatory potential component can be separated from the rest of the ERG components, since the process steps of the instant method are established based on the electrophysiological knowledge and findings described above.

Since parameters of the ERG data necessary to achieve clinical determinations can be obtained based on the oscillatory potential wave separated from the ERG waveform according to the invention as described above, the operator who detects the ERG does not have to manually process the obtained ERG data, by plotting lines on the obtained ERG waveform, as conventionally required. Further, the instant method eliminates a conventionally used electric filter for amplifying the OP component, which results in changing the original ERG waveform and makes it impossible to compare the obtained OP component waveform with the original ERG waveform. In other words, the instant method permits inspection of the extracted OP component waveform, and the original ERG waveform from which the OP component is separated immediately after the detection of the ERG waveform. Accordingly, the instant method of the invention has a wider range of clinical applications in the field of electrophysiological ERG analysis of the subject.

Further, the method of the present invention utilizes relatively a simple data-processing technique for obtaining moving averages of the processed ERG data and for differentiation of the same, and therefore allows for efficient clinical analysis during or immediately after the measurement or detection of an electroretinogram. Moreover, the present invention has made it possible to provide an improved automatic ERG measuring and analyzing system, which can contribute to the discovery of new electrophysiological relationships between the electroretinogram, and the ocular pathology or retinopathy and related diseases.

BRIEF DESCRIPTION OF THE DRAWINGS

The above and optional objects, features and advantages of the present invention will be better understood by reading the following detailed description of a presently preferred embodiment of the invention, when considered in connection with the accompanying drawings, in which:

FIG. 1 is a graph showing a waveform of an electroretinogram (ERG);

FIGS. 2(a) and 2(b) are graphs showing "a" and "b" waves of an ERG, and an oscillatory potential wave (OP wave) of the ERG, respectively, which are obtained by using a filter;

FIG. 6 is a graphical view showing an oscillatory potential component (OP component) of the ERG, which is tentatively determined by obtaining moving averages of the ERG;

FIG. 7 is a graph illustrating a manner in which a first peak and a tentative start point of the OP wave are determined;

FIG. 8 is a graph showing a manner in which a tentative OP-free waveform is obtained, based on the determined tentative start point;

DETAILED DESCRIPTION OF THE PREFERRED EMBODIMENT

To further clarify the principle of the present invention, the presently preferred embodiment of the invention will be described in detail, referring to the accompanying drawings.

Figure 3:
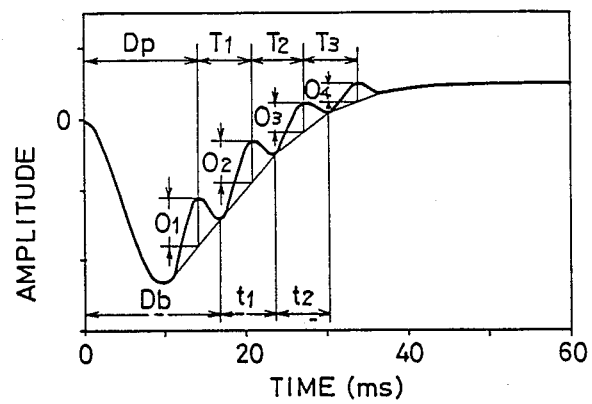
FIG. 3 is a graph illustrating various parameters of an OP wave, obtained by a manual processing of an ERG.
Figure 4:
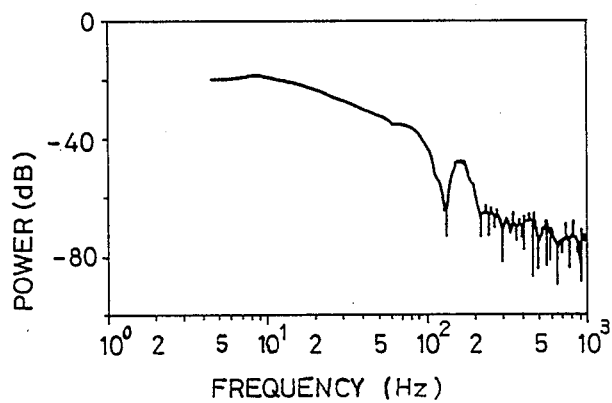
FIG. 4 is a graph showing a typical power spectrum of an ERG.
Figure 5:
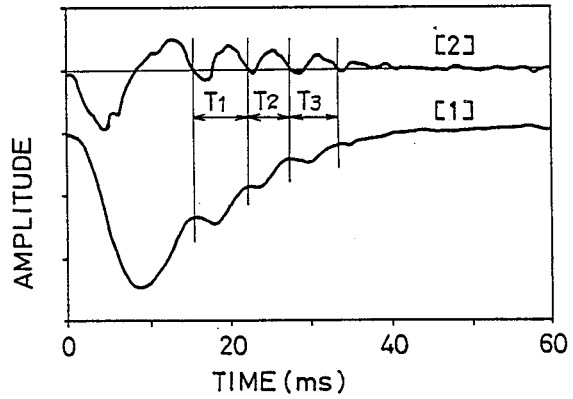
FIG. 5 is a graphical view indicating peak-to-peak distances of an OP wave, which are obtained by differentiation of an ERG.

By way of initial recognition, it is noted that an electroretinogram (ERG) consists of three major components: an "a" wave, a "b" wave and an oscillatory potential wave (OP wave), which have different latency times as defined above by reference to FIG. 3. The "a" and "b" waves have considerably smooth or gentle curves, as compared with that of the OP wave. The "a" and "b" waves overlapping each other cooperate to form negative peaks having comparatively high frequency components, and the composite frequency distribution of the "a" and "b" waves overlaps the frequency components of the OP wave, as indicated in FIG. 4. It is further recognized that the OP wave has a start point which is comparatively constant or non-fluctuating with respect to time, and has a comparatively high degree of periodicity within a relatively narrow range (i.e., a variation in the period of the OP wave is held within a relatively narrow range). Consequently, it is considered possible to eliminate the OP wave from the ERG, by practicing a simple method of obtaining moving averages of a portion of the ERG response data which follows the determined start point of the OP wave, so that the obtained moving averages provide a function performed by a notch filter. In view of the above recognitions, the method of the present invention was developed based on an assumption that the OP wave is a secondary damping oscillation whose initial phase is zero (0), and the principle of the invention requires a process of eliminating or filtering out the OP component from the ERG, according to the following steps (a) through (f):

(a) Initially, a detected ERG waveform indicated at [1] in FIG. 5 is differentiated into a waveform [2]. Peak-to-peak distances T1, T2 and T3 of the ERG waveform [1] due to the presence of the OP component overlapping the "b" wave are obtained based on zero-cross points of the differentiated ERG waveform [2]. An arithmetic mean of the peak-to-peak distances T1, T2 and T3 is calculated and defined as a mean period T of the OP wave to be extracted.

(b) Then, moving averages of the ERG waveform [1] are obtained based on the mean period T of the OP wave, whereby a waveform [3] indicated in FIG. 6 is obtained. The obtained waveform [3] is subtracted from the original ERG waveform [1], to extract a tentative OP component wave [4]. By "moving average" is meant an average performed on data in which the values closest to a given time are more heavily valued than others. To obtain the moving averages, a symmetric FIR (finite-impulse response) filter represented by the following equation is used. The equation is determined with phase characteristics of the ERG waveform [1] taken into account:

$$Y_k = \frac{1}{2N+1} \sum_{m=-N}^{N} X_{k+m}$$

where,
Yk: Averaged value
$X_{k+m}$: Discrete value
N: Number of samples

The waveform [3] of FIG. 6 obtained based on the obtained moving averages has an initial portion corresponding to a T/2 period following the start point, which portion is indefinite but is not a necessary data portion according to the invention. However, the moving-averaging process creates an influence on the two T/b 2 period portions which precede and follow the start point, respectively, since the OP wave is a signal having a certain latency time, that is, a delay time between the moment of light stimulation to the retina of the subject in question, and the moment at which the first peak appears. To eliminate this influence, the following steps are performed:

(c) Since it is presumed that the OP wave starts to appear with its zero (0) phase, the start point of the OP wave precedes the first peak, by a time equal to a quarter of the period T thereof. In this connection, it is noted that the first peak point of the OP wave based on the differentiated waveform [2] discussed above at (a) is influenced by the "b" wave. To eliminate this influence, a true first peak point P and a tentative start point A of the OP wave are first determined in the following manner. That is, the tentative OP component wave [4] (indicated in FIGS. 6 and 7) obtained in step (b) above is first differentiated into a waveform [5] of FIG. 7, and then the true first peak point P and the tentative start point A are determined based on the zero-cross points of the differentiated waveform [5], as shown in FIG. 7. The tentative start point A precedes the true first peak point P by the T/4 period.

(d) Successively, the portion of the ERG waveform [1] which follows the determined tentative start point A is rotated through 180° about the tentative start point A, whereby there is formed a first composite waveform [6] as shown in FIG. 8, which consists of the 180°-rotated portion of the ERG waveform [1] preceding the start point A, and the non-rotated portion of the ERG waveform [1] following the start point A. Then, moving averages of the thus obtained composite waveform [6] are obtained based on the period T, and a tentative OP-free waveform [7] containing no OP component is provided.

(e) A second composite waveform is prepared by connecting the initial portion of the original ERG waveform [1] which precedes the tentative start point A and which does not contain the OP component, and the portion of the OP-free waveform [7] which follows the tentative start point A. The thus prepared composite waveform does not contain the OP component.

The second composite waveform has a generally smooth or gentle curve. However, the curve of the second composite waveform may have a notched portion at the tentative start point A. This notched portion is caused by a deviation of the tentative start point A determined in step (c) above based on the mean period T of the OP wave, with respect to a true start point B. Such deviation of the tentative start point A from the true start point B occurs where the period of the first oscillation of the OP wave is different from the mean period T. To remove this deviation, the tentative start point A of the OP wave is shifted to a point A' in an advancing or retarding direction by a selected amount, and steps (d) and (e) are performed for this newly established tentative point. If the thus obtained second composite waveform does not have a sufficiently smooth curve, the tentative start point A is further shifted to a point A'', and steps (d) and (e) are performed. Similar operations are repeated until the curve of the second composite waveform becomes sufficiently smooth, namely, until the true start point B of the OP wave is detected.

Figure 9:
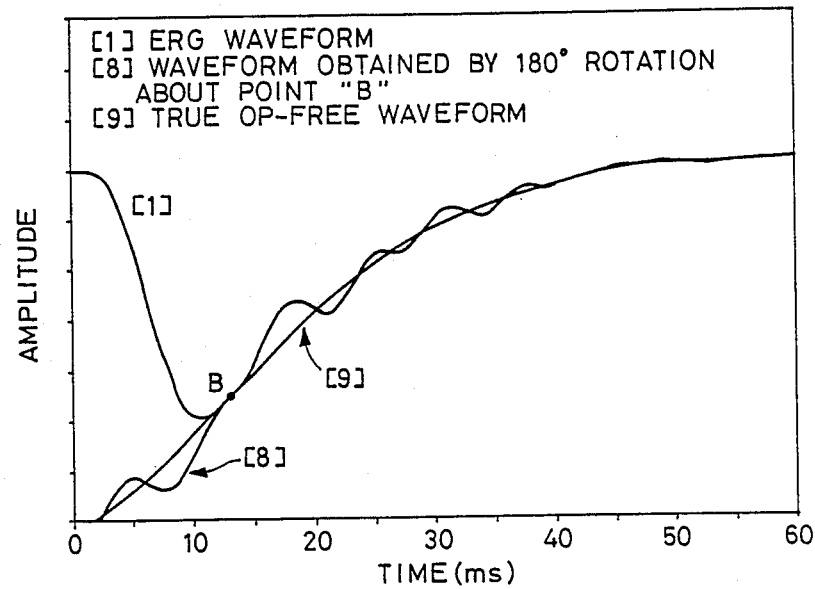
FIG. 9 is a graph showing a manner in which a true start point of the OP wave is determined by shifting the tentative start point.
Figure 10:
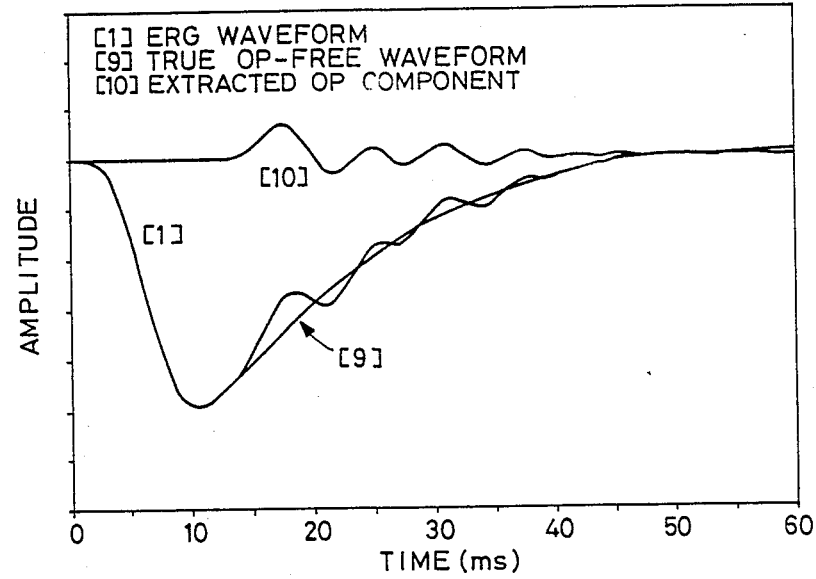
FIG. 10 is a graph showing a manner in which the OP component of the ERG is extracted from the originally detected ERG, based on the true start point.

(f) The ERG waveform is rotated about the detected true start point B, whereby a waveform [8] corresponding to the waveform [6] is obtained, as indicated in FIG. 9, in the same manner as described with respect to step (d) above in connection with the tentative OP-free waveform [7] of FIG. 8. Then, a true OP-free waveform [9] is obtained by obtaining moving averages of the waveform [8]. The true OP-free waveform [9] is subtracted from the original ERG waveform [1], whereby a desired waveform [10] consisting solely of the OP component is eventually extracted or separated from the original ERG waveform, as indicated in FIG. 10.

The shifting of the tentative start point A discussed above is not necessary, if the true OP-free waveform [9] is obtained at the initially determined start point A, i.e., if the true start point B is located at or sufficiently near the tentative start point A.

Figure 11:
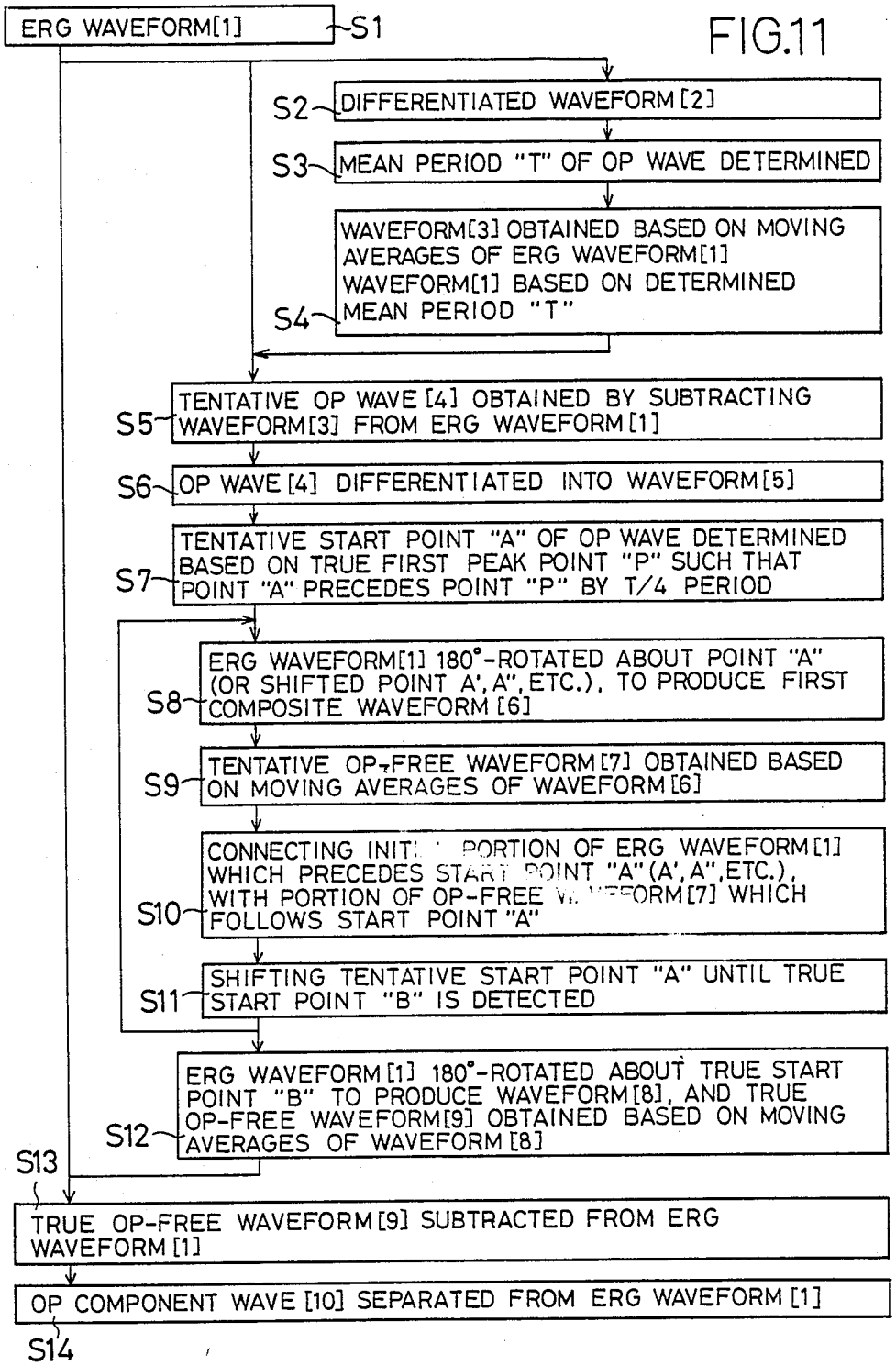
FIGS. 11 and 12 are detailed and simplified flow charts illustrating process steps for extracting the OP component, as shown in FIGS. 5 through 10.
Figure 12:
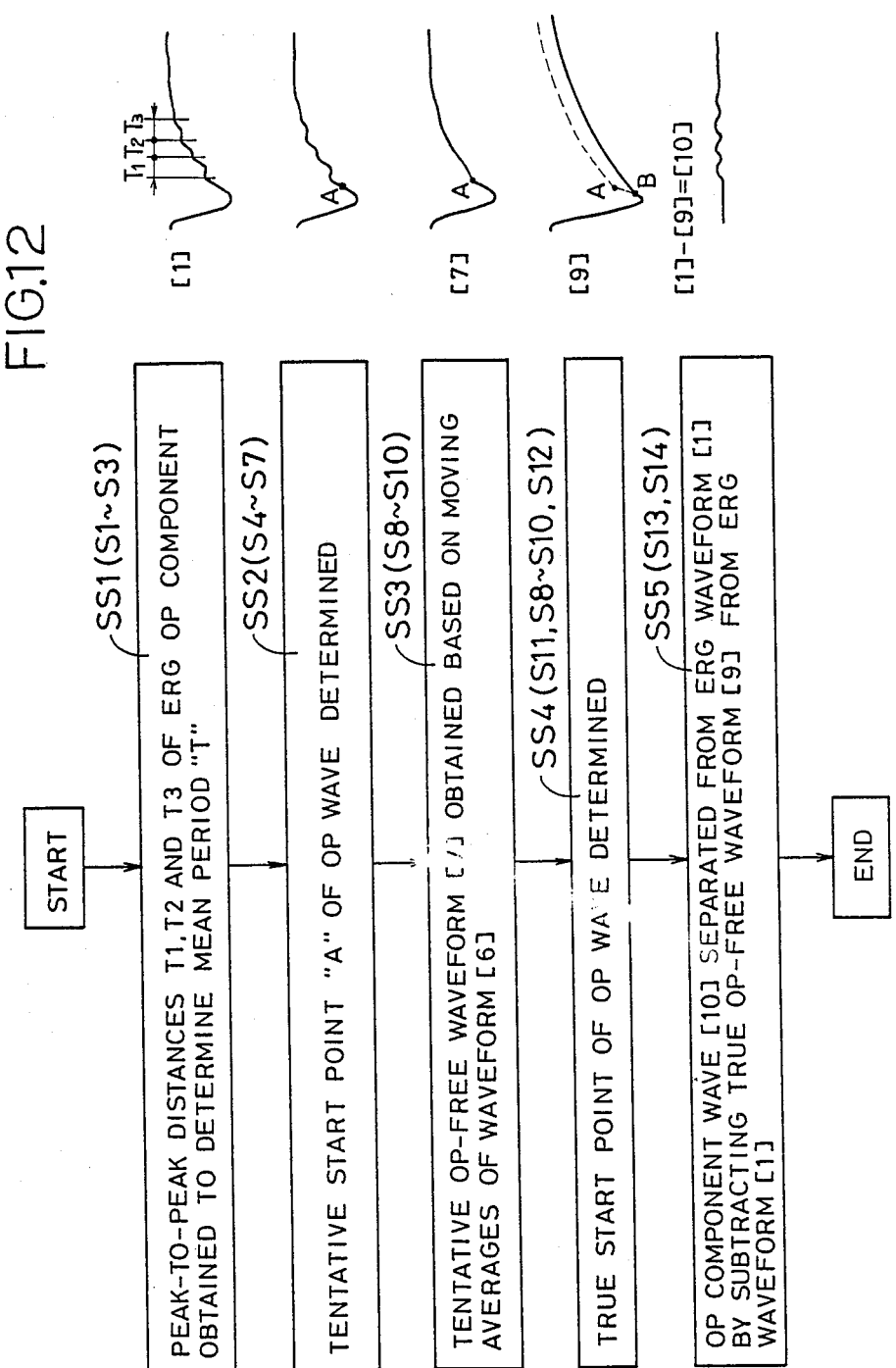

The above-described process steps of the presently preferred embodiment of the invention for separating or extracting the OP component from an ERG are illustrated in the flow chart of FIG. 11 in detail, and the flow chart of in FIG. 12 in a simplified manner.

Figure 13:
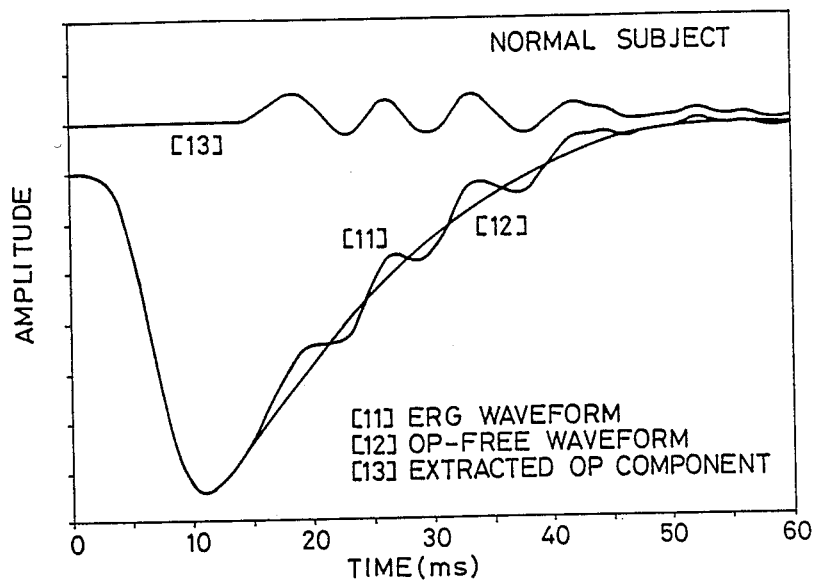
FIG. 13 is a graph showing an example of an extracted OP component of an ERG obtained from a normal subject.
Figure 14:
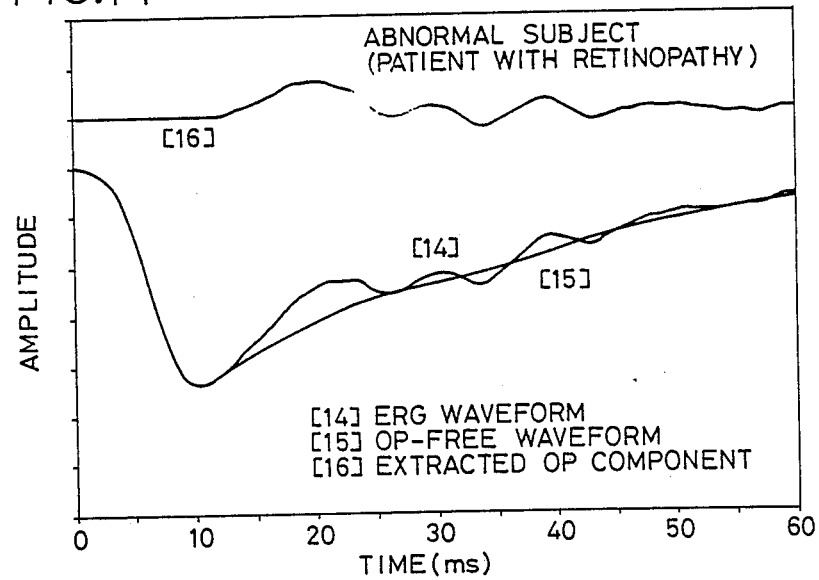
FIG. 14 is a graph showing an example of an extracted OP component of an ERG obtained from an abnormal subject.

Examples of OP component waves which were extracted from ERG waveforms of a normal and an abnormal subject according to the process steps described above are shown in FIGS. 13 and 14, respectively. The abnormal subject was a patient with a slight degree of retinopathy. The OP component wave [13] of the ERG of the normal subject shown in FIG. 13 has a comparatively large amplitude, while the OP component wave [16] of the ERG of the patient shown in FIG. 14 has a considerably reduced amplitude. Thus, the extracted OP component waves [13] and [16] correctly and clearly indicate the normal retina functioning of the normal subject, and the retinopathy of the patient, respectively.

Figure 15:
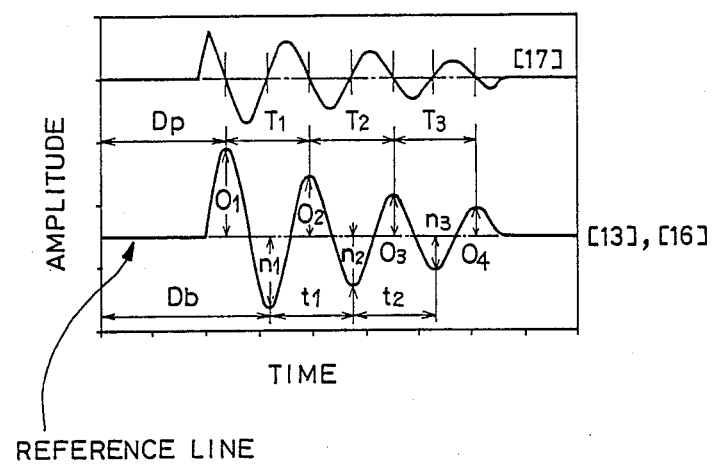
FIG. 15 is a graphical representation indicating characteristic parameters of the OP component obtained by differentiation thereof.

For further analysis of the extracted OP waves [13], [16] for more exact diagnosis of the retina condition or retinopathy, various parameters of the OP waves were obtained in the following manner. Namely, each of the OP waves [13], [16] was differentiated into a waveform as indicated at [17] in FIG. 15, and the peak points of the OP waves [13], [16] were detected based on the zero-cross points of the differentiated waveform [17]. Based on the detected peak points, latency times Dp and Db, and peak-to-peak distances T1–T3 or t1–t2 were obtained. Further, positive peak values or amplitudes O1–O4 between the oscillation peaks and a reference line, and negative peak values or amplitudes n1–n4 between the oscillation bottoms and the reference line were obtained. The thus obtained parameters were listed in Tables I and II below.

TABLE I

| | AMPLITUDE (V) | | | | | | |
|---|---|---|---|---|---|---|---|
| | O1 | O2 | O3 | O4 | n1 | n2 | n3 |
| Normal OP Wave [13] | 19.3 | 27.7 | 29.3 | 13.9 | 26.8 | 23.7 | 19.6 |
| Abnormal OP Wave [16] | 10.1 | 10.6 | 14.2 | 4.0 | 11.9 | 16.7 | 11.3 |

TABLE II

| | LATENCY | | PEAK-TO-PEAK DISTANCES | | | | |
|---|---|---|---|---|---|---|---|
| | Dp | Db | T1 | T2 | T3 | t1 | t2 |
| Normal OP Wave [13] | 16.8 | 20.5 | 6.8 | 5.9 | 8.2 | 6.8 | 7.3 |
| Abnormal OP Wave [16] | 20.9 | 23.6 | 6.4 | 8.2 | 7.3 | 6.8 | 6.4 |

The method according to the present invention as described above permits easy, efficient and accurate separation of an OP component from an ERG by using a simple data-processing technique for obtaining moving averages and for differentiation. The separated OP component and various parameters obtained from the OP components provide reliable diagnostic data for clinical applications. Thus, the present method has made it possible to provide an improved automatic ERG measuring and analyzing system having improved reliability and accuracy, which satisfies the practical clinical requirements.

While the present invention has been described in its presently preferred embodiment with a certain degree of particularity, it is to be understood that the invention is not limited to the precise details of the illustrated embodiment, but the invention may be embodied with various changes, modifications and improvements, which may occur to those skilled in the art, in the light of the foregoing teachings, without departing from the spirit and scope of the invention defined in the following claims.

What is claimed is:

1. A method of separating an oscillatory potential wave from an electroretinogram of a subject which contains an "a" wave, a "b" wave and said oscillatory potential wave that overlap each other, comprising:
   a first step of detecting said electroretinogram ([1]) which is produced by light stimulation to the retina of an eye of the subject;
   a second step of determining peak-to-peak distances of said electroretinogram, and thereby obtaining a mean period (T) of the oscillatory potential wave ([10]) to be separated from said electroretinogram;
   a third step of determining a tentative start point (A) of the oscillatory potential wave;
   a fourth step of obtaining an OP-free waveform ([7], [9]) free of said oscillatory potential wave, by obtaining moving averages of a first intermediate waveform ([6], [8]) which is determined based on said electroretinogram and the determined tentative start point (A); and
   a fifth step of extracting said oscillatory potential wave ([10]) by subtracting said OP-free waveform ([7], [9]) from said electroretinogram ([1]).

2. A method according to claim 1, wherein said second step comprises differentiating said electroretinogram ([1]), determining said peak-to-peak distances (T1, T2, T3) based on zero-cross points of the differentiated electroretinogram ([2]), and obtaining said mean period (T) by obtaining an arithmetic mean of said peak-to-peak distances.

3. A method according to claim 1, wherein said third step comprises:
   preparing a second intermediate waveform ([3]) by obtaining moving averages of said electroretinogram ([1]) based on said determined mean period (T);
   obtaining a tentative oscillatory potential component wave ([4]) by subtracting said second intermediate waveform ([3]) from said electroretinogram ([1]);

differentiating said tentative oscillatory potential component wave ([4]) into a third intermediate waveform ([5]); and determining a first peak point (P) of said oscillatory potential wave ([10]) based on a zero-cross point of said third intermediate waveform ([5]), and determining said tentative start point (A) which precedes the determined first peak point (P) by a quarter of said mean period (T).

4. A method according to claim 1, wherein said fourth step comprises:
(i) rotating a portion of said electroretinogram ([1]) following said tentative start point (A), through 180° about said tentative start point (A);
(ii) preparing a first composite waveform ([6]) which consists of said portion of the electroretinogram ([1]) which has been rotated through 180° and which precedes said tentative start point (A), and the portion of the electroretinogram ([1]) which is not rotated and which follows said tentative start point (A);
(iii) obtaining moving averages of said first composite waveform ([6]) based on said determined mean period (T), and obtaining said OP-free waveform ([7], [9]) based on the obtained moving averages; and
(iv) preparing a second composite waveform ([1]+[7], [9]) which consists of said initial portion of said electroretinogram ([1]), and a portion of said OP-free waveform ([7], [9]) which follows said tentative start point (A).

5. A method according to claim 4, wherein if said second composite waveform ([1]+[9]) has a sufficiently gentle curve, said tentative start point (A) is determined as a true start point (B), and if said second composite waveform ([1]+[7]) has a notched portion at said tentative start point (A), the start point (A) is shifted by a selected amount, and operations similar to the operations (i)–(iv) of said fourth step recited in claim 4 are repeated for the shifted start point, the shifting of the start point (A) and said operations similar to operations (i)–(iv) being repeated until there is obtained said true start point (B) at which said second composite waveform ([1]+[9]) has said sufficiently gentle curve.

6. A method according to claim 1, further comprising the steps of differentiating said extracted oscillatory potential wave ([10]), determining peak points of said extracted oscillatory potential wave ([10]) based on zero-cross points of the differentiated oscillatory potential wave ([17]), and obtaining parameters which include latency times (Dp, Db), peak-to-peak distances (T1, T2, T3, t1, t2), and peak values (O1, O2, O3, O4, n1, n2, n3) of the extracted oscillatory potential wave ([10]).

* * * * *